United States Patent [19] [11] 4,104,312
Angstadt et al. [45] Aug. 1, 1978

[54] OXIDATION OF OLEFINS WITH ORGANOMETALLIC COMPLEX CATALYSTS

[75] Inventors: Howard P. Angstadt, Media; William P. Griffin, Jr., Pittsburgh, both of Pa.

[73] Assignee: Sun Ventures, Inc., St. Davids, Pa.

[21] Appl. No.: 526,036

[22] Filed: Nov. 21, 1974

Related U.S. Application Data

[63] Continuation-in-part of Ser. No. 777,493, Nov. 20, 1968.

[51] Int. Cl.² ............................................ C07C 179/04
[52] U.S. Cl. .................................................. 260/610 B
[58] Field of Search ......................... 260/610 B, 610 A Primary Examiner—James O. Thomas, Jr.
Assistant Examiner—Werren B. Lone
Attorney, Agent, or Firm—J. Edward Hess; Donald R. Johnson; Stanford M. Back

[57] ABSTRACT

Organometallic complexes formed between hexaalkylphosphoramides (HAPA) and transition metal salts, including rare earth metals, have been found to be effective catalysts for the oxidation of olefins to form valuable oxidation products, particularly the corresponding hydroperoxides.

11 Claims, No Drawings

OXIDATION OF OLEFINS WITH ORGANOMETALLIC COMPLEX CATALYSTS

CROSS-REFERENCE TO RELATED APPLICATIONS

This application is a continuation-in-part of U.S. Ser. No. 777,493, filed Nov. 20, 1968.

Related application, Ser. No. 772,421, filed Oct. 31, 1968, in the name of Angstadt et al discloses the oxidation of alkylaromatic compounds wherein novel complexes formed between a hexaalkylphosphoramide and metal salts are employed as the oxidation catalysts. Certain of the catalysts disclosed therein are also useful in the present invention.

This application is also related to the following applications:

| Serial No. | Applicant | File Date |
|---|---|---|
| 773,633 | Angstadt et al | 11/05/68 |
| 787,582 | Angstadt | 12/27/68 |
| 801,187 | Angstadt | 2/20/69 |
| 853,547 | Angstadt | 8/27/69 |

The entire disclosure of all of the above six cases is hereby incorporated herein by reference.

BACKGROUND OF THE INVENTION

This invention relates to a novel process for the oxidation of olefins to form various oxidation products, particularly hydroperoxides, or the decomposition products thereof, i.e. alcohols, ketones, aldehydes, epoxides and the like, or mixtures thereof. More particularly, this invention is directed to the use of complexes formed by reacting metal salts with an hexaalkylphosphoramide (hereinafter HAPA) as oxidation catalysts in the aforesaid process, including those complexes formed between HAPA and lanthanide and actinide metal salts. The term "lanthanide metal salts" is intended to include the metal lanthanum as well as other metals in this series.

It is an object of this invention, therefore, to provide a novel process for the oxidation of olefin compounds whereby the oxidation rate, or the selectivity, or both, may be increased, particularly with respect to the formation of the corresponding hydroperoxides.

SUMMARY OF THE INVENTION

It has now been found, in accordance with the present invention, that organometallic complexes formed between metal salts, preferably those derived from transition metals (including metals of the lanthanide and actinide series), and hexaalkylphosphoramides are effective catalysts in the oxidation of olefins. Certain of these catalysts are especially effective in forming the hydroperoxides of olefins to the exclusion of other oxidation products. Throughout this description it will be understood that the term "lanthanide series" is meant to include the metal lanthanum itself as well.

DESCRIPTION OF THE INVENTION

The organometallic catalysts employed in the process of this invention, namely, the metal salts HAPA complexes, may be represented by the general formula $$MX_n(HAPA)_m$$

where M is a metal cation, preferably a transition metal from groups IIB, IIIB, IVB, VB, VIB, VIIB, VIIIB, IB, IIA or IIB of the periodic table, including the lanthanides and actinides; HAPA is an hexaalkylphosphoramide having the formula

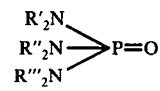

wherein each of R', R", and R''' is an alkyl group of from 1 to 30 carbon atoms, preferably containing 1 to 4 carbon atoms, and wherein each group may be the same or different; X is the anion of the metal salt, $m$ is an integer of from 1 to 8; and $n$ is an integer of from 1 to 4.

These complexes may be prepared in accordance with the teachings of *Inorganic Chemistry*, I, 866-872 (1962) wherein is described the complexing of hexamethylphosphoramide (HMPA) with the perchlorate salts of zinc, cobalt and nickel. Briefly, the preparation of these compounds may readily be achieved by mixing a hydrate of the metal salt with an excess of an HAPA and recovering the resultant crystals in a known manner. Alternatively, the complex may be prepared by first dissolving the metal salt in an excess of solvent, preferably an alkanol such as t-butanol, to which solution is added an excess of HAPA, followed by routine recovery and drying of the resulting precipitate. In some instances the complex does not form a solid which can be recovered readily, if at all, in which case the resulting solution may satisfactorily be employed instead. These organometallic complexes may be employed either as the purified solid or in solution with excess HAPA itself as the preferred solvent therefor.

These metal complexes give yields of hydroperoxides at conversion rates of from about 4 to 20 percent per hour. In the case of those metal complexes which yield little or no amounts of hydroperoxides in the final product, but which do yield other oxidation products, this is because the hydroperoxides which are first formed are then rapidly decomposed by the catalyst complex itself to form, e.g., alcohols, aldehydes, or ketones. Thus, for example, where oxidation is effected as shown by $O_2$ uptake yet no hydroperoxide or only minor amounts are found, there are also recovered in the reaction mixture the corresponding alcoholic and/or ketonic olefins and the like.

That is to say, since the known mechanism for the autoxidation of alkyl aromatic compounds includes the homolytic cleavage of the first formed intermediate, i.e. the hydroperoxide, it is recognized that catalysts which accelerate this oxidation will also accelerate the decomposition of this intermediate. Hence it is possible to autoxidize the hydrocarbon to oxidized products without being able to detect the hydroperoxide intermediate because it is being decomposed to other oxidation products as rapidly as it is being formed. Therefore, the fact that no hydroperoxide is detected in the product does not mean it was not formed; it simply means that the catalyst is very effective in further converting this intermediate to aldehydes, ketones, alcohols, etc. In fact, the participation of hydroperoxides in the autoxidation of these hydrocarbons is so well established in the chemical literature that no other mechanistic pathways are seriously considered. See, for example, G. A. Russell, J.A.C.S. 77, 4583-90, (1955); H. S. Blanchard, J.A.C.S. 82, 2014-21, (1959); J. A. Howard et al, *Canadian Jour. Chem.* 45 785-792 (1966); inter alia.

Thus, it will be evident to those skilled in the art that the exact nature of the oxidation product can readily be determined by routine experimentation with various catalyst, but that in all cases it will be either an hydroperoxide and/or the decomposition products thereof as shown in the above-cited art, depending upon the exact catalyst composition chosen.

The metal salts used in forming the organometallic complexes are as stated above, any metals of the periodic table, and preferably those derived from transition metals of groups IIIB, IVB, VB, VIB, VIIB, VIIIB, IB, IIA and IIB including the lanthanide and actinide metals.

The nature of the anion, X, is not critical, but may include any of the following inorganic or organic groups:

| | | | |
|---|---|---|---|
| $CN^-$ | cyanide | $AsO_3^=$ | arsenite |
| $NC^-$ | isocyanide | $AsO_4^=$ | arsenate |
| $CN_2^=$ | cyanamide | $C_2H_3O_2^-$ | acetate* |
| $OCN^-$ | cyanate* | $C_4H_4O_6^=$ | tartrate |
| $CNO^-$ | isocyanate* | $C_7H_5O_2^-$ | benzoate |
| $ClO^-$ | chlorite | $B_4O_7^=$ | tetraborate |
| $ClO_3^-$ | chlorate | $BrO_3^-$ | bromate |
| $SCN^-$ | thiocyanate | $Cr_2O_7^=$ | dichromate |
| $CNS^-$ | isothiocyanate | $F^-$ | fluoride |
| $SeCN^-$ | selenocyanate | $CH_2O^-$ | formate |
| $S_2O_3^=$ | thiosulfate | $SeO_3^=$ | selenide |
| $SO_3^=$ | sulfite | $SeO_4^=$ | selenate |
| $SO_4^=$ | sulfate | $C_6H_5O^-$ | phenoxide |
| $S^-$ | sulfide | $C_2O_4^=$ | oxalate* |
| $HS^-$ | hydrosulfide | $O^=$ | oxide |
| $TeCN$ | tellurocyanate | $TeO_3^=$ | tellurite |
| $OCl^-$ | oxychloride | $AsS_3^=$ | thioarsenite |
| $OH^-$ | hydroxide | $AsS_4^=$ | thioarsenate |
| $NO_2^-$ | nitrite* | $Cl^-$ | chloride* |
| $PO_3^{\equiv}$ | phosphite | $Br^-$ | bromide* |
| $PO_4^{\equiv}$ | phosphate* | $NO_3^-$ | nitrate* |
| $CrO_4^=$ | chromate | $CO_3^=$ | carbonate* |
| $BO_3^{\equiv}$ | borate | $ClO_4^=$ | perchlorate* | in which those marked with an asterisk are most preferred.

As mentioned hereinabove, the oxidation products of the instant process are hydroperoxides, or the decomposition products thereof, i.e., alcohols, ketones, aldehydes, epoxides or mixtures thereof. Of these various products, maximization of the formation of the hydroperoxides is generally preferred inasmuch as these compounds are especially useful in facilitating the drying capabilities of polymers, i.e., they are useful as siccative agents.

The olefins employed as the starting materials in this process include any straight or branched chain unsaturated compound having at least one hydrogen atom on the α- carbon atom, such as octene-1, and the like, as well as cyclic olefins having at least one hydrogen atom on the α- carbon atom, such as cyclohexene, cyclooctadiene, α-pinene, d-limonene and the like. These olefins may contain substituent groups which are nonreactive under the conditions of this process, as for example, ester, halo, nitro, alkyl or like groups which remain as substituents of the final product.

The process of this invention is conveniently carried out by the rapid passage of air or oxygen through a suitable reactor, to which has first been added a solution of the olefin and organometallic catalyst. The solvent for the reaction is preferably an excess amount of the starting material, although other solvents which are inert to the reaction of peroxidation may likewise be employed.

The air or oxygen should desirably be brought into intimate contact with the liquid phase with vigorous agitation, either mechanically or by the use of high speed stirrers, or by aeration using suitable nozzles or the like.

Mechanical agitation has been found to be particularly effective in those cases where the rate at which the oxygenating gas is introduced into the reactor is low, i.e., below about 3 liters per hour. Thus, for example, when air is merely introduced at the surface of the reaction mixture, agitation by a commercially available reciprocating disc type stirrer (e.g., "Vibro-Mixer", Chemapec, Inc., Hoboken, New Jersey, U.S.A.) has been found to increase the rate of oxidation per hour by as much as four-fold over what is obtained with lesser amounts of agitation.

Alternatively, these increased rates may similarly be achieved, and mechanical agitation substantially or entirely dispensed with, by appreciably increasing the rate at which air or oxygen is introduced into the reaction medium. This is preferably accomplished by bubbling the oxygenating gas through the reaction mixture vigorously, desirably in such a manner as to insure maximum dispersal of the gas through the medium, as for example, by using fritted glass discs or the like. Depending upon the amount of liquid medium involved, the rate of oxygenating gas my thus vary from about 0.5 to 300 liters per hour.

The amount of catalyst employed will vary depending upon the nature and amount of material to be oxidized and the particular catalyst employed. In general, however, from about 0.1 to 5.0 parts by weight of catalyst per 100 parts of substrate and preferably from 0.5 to 1.5 parts per 100 parts has been found to be satisfactory.

The rate of input of oxygen or air will likewise vary depending upon the reaction temperature and pressure employed. There should be provided an amount at least theoretically sufficient to convert the alkyl aromatic compound to the corresponding hydroperoxide, and preferably an excess of this amount. In general, a flow rate ranging from as little as 0.5 to 300 liters per hour is sufficient for most conversions as described above, and preferably at least 3 liters per hour. While the reaction preferably carried out at atmospheric pressure, it is possible to employ an oxygen pressure of from about 0.2 atmospheres to 50 atmospheres, and preferably about 1 to 10 atmospheres. At these higher pressures the oxidation rate is found to increase substantially when the organometallic complexes are employed, and particularly those catalysts which are selective for hydroperoxide formation.

The reaction temperature may range from about 50° to 150° C, and preferably from 90° to 120° C. At temperatures above 150° C the catalysts tend to be thermally unstable.

The reaction is generally run from half an hour to ten hours, depending upon the amount of substrate employed and the degree of conversion desired. When, however, a hydroperoxide is the principal product being formed, it is desirable that the reaction be terminated after a period of 1 to 6 hours at which point the reaction rate usually begins to taper off.

If desired, and advantageous, small amounts of the hydroperoxide corresponding to the desired product may be introduced into the reaction medium to act as a reaction initiator. The amount of the hydroperoxide to be added is not critical, but 0.1 percent to 1.0 percent by weight of the starting material is preferred. It should be understood however, that the addition of any such initiator will not change the nature of the product that would otherwise be obtained; the initiator serves only to reduce the induction time of the reaction.

The resulting products are readily recovered from the reaction medium by conventional methods. Thus, for example, a hydroperoxide may be conveniently recovered by isolating it as its sodium salt by addition of concentrated aqueous NaOH to the reaction product, followed by separation and drying of the hydroperoxide salt.

In the following examples, unless otherwise noted, both rate of conversion of the starting material and selectivity of the catalyst for converting the starting material to the corresponding hydroperoxide were measured. To measure rate of conversion, regardless of the nature of the oxidation product, the amount of oxygen uptake in a closed system was used as measure of the amount of oxidation which took place; to measure the amount of hydroperoxide formed, samples of the reaction medium were periodically withdrawn and iodometrically titrated to determine the hydroperoxide content. On the basis of both of these figures the selectivity of any given catalyst for the formation of hydroperoxide could then be routinely determined.

EXAMPLE 1

The metal salt HAPA catalyst useful in the present invention may be prepared in accordance with either of the following two methods, wherein manganese and various lanthanide metal salts and hexamethylphosphoramide are used by way of illustration:

Lanthanum chloride hydrate (2 g.) was warmed in a test tube with a 5 molar excess of HMPA. The warming was continued until all of the salt was in solution. Upon cooling, a white substance was crystallized, filtered out and dried on a clay plate. This substance analyzed correctly for carbon and hydrogen for a compound of the formula $LaCl_3.3HMPA.XH_2O$ where X is one or two. The infrared spectra showed a P=O absorption displaced from 1210 $cm^{-1}$ in agreement with the existing literature data.

In accordance with the foregoing procedure, but substituting $MnBr_2$ for $LaCl_3$ there was obtained the corresponding $MnBr_2.2HMPA$.

Alternatively, one can dissolve the hydrated metal salts in an excess of 2,2-dimethoxypropane to obtain a solution of the anhydrous salt in acetone and methanol. By adding an HAPA to this solution and evaporating this solvent under nitrogen, one obtains as a crystalline residue the anhydrous metal salt HAPA complex. Thus, for example, in accordance with the foregoing procedure, but substituting $PrCl_3$ and $SmCl_3$ for $LaCl_3$ there was obtained the corresponding $PrCl_3.3HMPA$ and $SmCl_3.3HMPA$ respectively.

By employing either of the foregoing procedures, but substituting other metal salts, as desired, for those employed above, additional catalyst complexes useful in the process of the present invention may likewise be routinely prepared.

EXAMPLE 2

8.2 g. (100 m moles) of cyclohexene was placed in a flask and rapidly stirred by a Vibro-Mixer with 57.3 mg. of $MnBr_2.2HMPA$ and 0.2 cc of cumene hydroperoxide. The flask was immersed in a 60° C oil bath, connected to an oxygen buret and the oxygen opened to the system. At the end of one hour 13 percent of the cyclohexene had been converted to cyclohexene hydroperoxide as determined by $O_2$ volume consumed and iodometric titration. At the end of the second hour 17 percent had been converted. In the absence of the catalyst the general literature in the area indicates a conversion of about 1 percent would be expected [J. Am. Chem. Soc. 87, 4826 (1965)].

When lanthanum chloride-HMPA complex was used in place of manganese bromide HMPA, 7 percent conversion after two hours was observed. The product was mostly the hydroperoxide of cyclohexene.

EXAMPLES 3 - 8

In accordance with the procedure of Example 2, but substituting the following olefins for cyclohexene, and employing the catalysts listed below at 100° C, there was obtained the following results:

| EXAMPLE | OLEFIN | CATALYST | CONVERSION (Percent) | | SELECTIVITY FOR THE HYDROPEROXIDE (Percent) |
|---|---|---|---|---|---|
| | | | 1st Hour | 2nd Hour | |
| 3 3 | α-pinene | $MnBR_2.2HMPA$ | — | 27.0 | 14 |
| 4 | cyclooctadiene | $MnBr_2.2HMPA$ | — | 15.0 | 8 |
| 5 | octene-1 | $MnBr_2.2HMPA$ | 3.0 | — | 0 |
| 6 | α-pinene | $LaCl_3.3HMPA$ | 16.5 | 18.1 | 41 (2nd hour) |
| 7 | α-pinene | None | 12.8 | 16.3 | 48 (2nd hour) |
| 8 | cycloheptene | — | 7.3 | — | 36 |

EXAMPLE 9

In accordance with the procedure of Example 2, 29.4 g. of the methyl ester of linoleic acid was placed in a flask and rapidly stirred with 57.3 mg. of $MnBr_2.2HMPA$ and 0.2 cc of cumene hydroperoxide. The flask was immersed in an oil bath at 100° C, connected to an oxygen buret and the oxygen opened to the system. At the end of one hour 14.7 percent of the acid ester had been oxidized while at the end of the second hour 16.1 percent conversion was measured. The products comprised a mixture of the corresponding unsaturated ketonic and alcoholic esters; no hydroperoxide was found in the product mixture.

EXAMPLE 10

The procedure of Example 9 was repeated except that 60 mg. of $LaCl_3.3HMPA$ is substituted for the corresponding manganese bromide complex of Example 8. After the first hour the percentage conversion of the starting material is determined to be 45 percent. Selectivity for the hydroperoxide at the end of that period is measured at 37 percent. The product contained not only the corresponding hydroperoxide of the acid ester, but also a mixture of the aforementioned unsaturated ketonic and alcoholic esters.

EXAMPLE 11

According to the procedure of Example 2, 13.6 g. of limonene is oxidized using $La(NO_3)_3.HMPA$ complex as the catalyst. After one hour a 20% conversion of the limonene is observed with a selectivity for the corresponding hydroperoxide of 40%. The rest of the product mixture consists of further oxidized products, i.e., the corresponding limonenol and some ketone.

EXAMPLE 12

In accordance with the procedure of Example 2, methylcyclohexene is rapidly stirred with $Ce(C_2O_4)_2 \cdot HMPA$ at 70° C for 1 hour. At that time 8% of the methylcyclohexane is converted to the corresponding hydroperoxide.

The invention claimed is:

1. In the process for the catalytic oxidation of aliphatic or alicyclic olefins having at least one hydrogen atom on the α-carbon atom, said olefins having from 3 to 19 carbon atoms, in the presence of air or oxygen at a temperature of from about 50° to 150° C to form hydroperoxides, the decomposition products thereof, or mixtures of the same, the improvement wherein the catalyst is of the formula $$MX_n(HAPA)_m$$

wherein HAPA is a hexaalkylphosphoramide, the alkyl moiety of which has from one to four carbon atoms; MX is a metal salt wherein M is a transition metal cation of Group IB, IIB, IIIB, IVB, VB, VIB, VIIB, VIIIB or IIA of the Periodic Table and X is the anion of said metal salt; $m$ is an integer of from 1 to 8; and $n$ is an integer of from 1 to 4, wherein the ratio of said catalyst to said olefin is from about 0.1 to 5.0 parts by weight of catalyst per 100 parts by weight of olefin.

2. The process according to claim 1 wherein the reaction is carried out under vigorous agitation.

3. The process according to claim 1 wherein the air or oxygen is introduced at a rate of from about 0.5 to 300 liters per hour.

4. The process according to claim 1 wherein the ratio of catalyst to olefin is in the range of from 0.5 to 1.5 parts by weight of catalyst per 100 parts of substrate.

5. The process according to claim 1 wherein the reaction is carried out at a temperature of from 90° to 120° C.

6. The process according to claim 1 wherein the oxidation is carried out at an oxygen pressure of from 0.2 to 50 atmospheres.

7. The process according to claim 1 wherein the oxidation is carried out in the added presence of a hydroperoxide initiator.

8. The process according to claim 1 wherein the metal is of the lanthanide or actinide series.

9. The process according to claim 1 wherein the anion is a bromide, chloride, carbonate, nitrate or perchlorate.

10. The process according to claim 1 wherein the anion is a cyanide, cyanate, isocyanate, nitrite, phosphate, acetate or oxalate.

11. The process according to claim 1 wherein the hydroperoxide decomposition products are alcohols, aldehydes, ketones, or mixtures thereof.

* * * * *